(12) United States Patent
Bolin et al.

(10) Patent No.: US 7,939,569 B1
(45) Date of Patent: May 10, 2011

(54) ANILINE ANALOGS AS GLYCOGEN SYNTHASE ACTIVATORS

(75) Inventors: David Robert Bolin, Montclair, NJ (US); Matthew Michael Hamilton, Hackettstown, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/908,176

(22) Filed: Oct. 20, 2010

Related U.S. Application Data

(60) Provisional application No. 61/265,476, filed on Dec. 1, 2009.

(51) Int. Cl.
C07C 211/00 (2006.01)
A01N 33/18 (2006.01)
(52) U.S. Cl. ........................................ 514/741; 564/305
(58) Field of Classification Search .................. None
See application file for complete search history.

(56) References Cited

U.S. PATENT DOCUMENTS
2004/0266856 A1 12/2004 Chu et al.

FOREIGN PATENT DOCUMENTS
WO 2004058679 7/2004
WO 2006058648 6/2006

OTHER PUBLICATIONS
Yamaguchi et al., caplus an 2008:476100.*

* cited by examiner

Primary Examiner — Sun Jae Y Loewe
(74) Attorney, Agent, or Firm — George W. Johnston; Dennis P. Tramaloni; Samuel H. Megerditchian

(57) ABSTRACT

Provided herein are compounds of the formula (I):

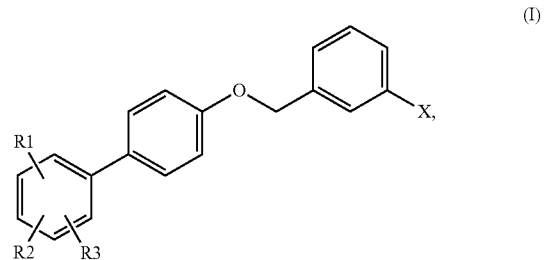

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

24 Claims, No Drawings

ANILINE ANALOGS AS GLYCOGEN SYNTHASE ACTIVATORS

PRIORITY TO RELATED APPLICATION(S)

This application claims the benefit of U.S. Provisional Application No. 61/265,476, filed Dec. 1, 2009, which is hereby incorporated by reference in its entirety.

FIELD OF THE INVENTION

The invention is directed to compounds, salts and pharmaceutical compositions useful as activators of glycogen synthase for the treatment of metabolic diseases and disorders.

All documents cited or relied upon below are expressly incorporated herein by reference.

BACKGROUND OF THE INVENTION

Diabetes mellitus is a common and serious disorder, affecting 10 million people in the U.S. [Harris, M. I. Diabetes Care 1998 21 (3S) Supplement, 11C], putting them at increased risk of stroke, heart disease, kidney damage, blindness, and amputation. Diabetes is characterized by decreased insulin secretion and/or an impaired ability of peripheral tissues to respond to insulin, resulting in increased plasma glucose levels. The incidence of diabetes is increasing, and the increase has been associated with increasing obesity and a sedentary life. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. However, these factors are often unable to control the disease, and there are a number of drug treatments available, including insulin, metformin, sulfonylureas, acarbose, and thiazolidinediones. Each of these treatments has disadvantages and there is an ongoing need for new drugs to treat diabetes.

Metformin is an effective agent that reduces fasting plasma glucose levels and enhances the insulin sensitivity of peripheral tissue, mainly through an increase in glycogen synthesis [De Fronzo, R. A. Drugs 1999, 58 Suppl. 1, 29]. Metformin also leads to reductions in the levels of LDL cholesterol and triglycerides [Inzucchi, S. E. JAMA 2002, 287, 360]. However, it loses its effectiveness over a period of years [Turner, R. C. et al. JAMA 1999, 281, 2005].

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [Tadayyon, M. and Smith, S. A. Expert Opin. Investig. Drugs 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [Inzucchi, S. E. JAMA 2002, 287, 360] and, like metformin, they lose efficacy over time [Turner, R. C. et al. JAMA 1999, 281, 2005]. A further problem often encountered in patients treated with sulfonylureas is hypoglycemia [Salas, M. and Caro, J. J. Adv. Drug React. Tox. Rev. 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [Inzucchi, S. E. JAMA 2002, 287, 360].

Because none of these treatments is effective over the long term without serious side effects, there is a need for new drugs for the treatment of type 2 diabetes.

In skeletal muscle and liver, there are two major pathways of glucose utilization: glycolysis, or oxidative metabolism, where glucose is oxidized to pyruvate; and glycogenesis, or glucose storage, where glucose is stored in the polymeric form glycogen. The key step in the synthesis of glycogen is the addition of the glucose derivative UDP-glucose to the growing glycogen chain, and this step is catalyzed by the enzyme glycogen synthase [Cid, E. et al. J. Biol. Chem. 2000, 275, 33614]. There are two isoforms of glycogen synthase, found in liver [Bai, G. et al. J. Biol. Chem. 1990, 265, 7843] and in other peripheral tissues including muscle [Browner, M. F. et al. Proc. Nat. Acad. Sci. U.S.A. 1989, 86, 1443]. There is clinical and genetic evidence implicating both forms of glycogen synthase in metabolic diseases such as type 2 diabetes and cardiovascular disease. Both basal and insulin-stimulated glycogen synthase activity in muscle cells from diabetic subjects were significantly lower than in cells from lean non-diabetic subjects [Henry, R. R. et al. J. Clin. Invest. 1996, 98, 1231-1236; Nikoulina, S. E. et al. J. Clin. Enocrinol. Metab. 2001, 86, 4307-4314]. Furthermore, several studies have shown that levels of muscle [Eriksson, J. et al. N. Engl. J. Mod. 1989, 331, 337; Schulman, R. G. et al. N. Engl. J. Med. 1990, 332, 223; Thorburn, A. W. et al. J. Clin. Invest. 1991, 87, 489] and liver [Krssak, M. et. al. Diabetes 2004, 53, 3048] glycogen are lower in diabetic patients than in control subjects. In addition, genetic studies have shown associations in several populations between type 2 diabetes and/or cardiovascular disease and mutation/deletion in the GYS1 gene encoding the muscle isoform of glycogen synthase [Orhu-Melander, M. et al. Diabetes 1999, 48, 918; Fredriksson, J. et. al. PLoS ONE 2007, 3, e285; Kolhberg G. et. al. N. Engl. J. Med. 2007, 357, 1507]. Patients lacking GYS2 encoding the liver isoform of glycogen synthase, suffer from fasting ketotic hypoglycemia and postprandial hyperglycemia, hyperlactanemia and hyperlipidemia, supporting the essential role of liver GS in maintaining normal nutrient metabolism. [Weinstein, D. A. et. al. Mol. Genetics and Metabolism, 2006, 87, 284]

Glycogen synthase is subject to complex regulation, involving phosphorylation in at least nine sites [Lawrence, J. C., Jr. and Roach, P. J. Diabetes 1997, 46, 541]. The dephosphorylated form of the enzyme is active. Glycogen synthase is phosphorylated by a number of enzymes of which glycogen synthase kinase 3P (GSK3β) is the best understood [Tadayyon, M. and Smith, S. A. Expert Opin. Investig. Drugs 2003, 12, 307], and glycogen synthase is dephosphorylated by protein phosphatase type I (PP1) and protein phosphatase type 2A (PP2A). In addition, glycogen synthase is regulated by an endogenous ligand, glucose-6-phosphate which allosterically stimulates the activity of glycogen synthase by causing a change in the conformation of the enzyme that renders it more susceptible to dephosphorylation by the protein phosphatases to the active form of the enzyme [Gomis, R. R. et al. J. Biol. Chem. 2002, 277, 23246].

Several mechanisms have been proposed for the effect of insulin in reducing blood glucose levels, each resulting in an increase in the storage of glucose as glycogen. First, glucose uptake is increased through recruitment of the glucose transporter GLUT4 to the plasma membrane [Holman, G. D. and Kasuga, M. Diabetologia 1997, 40, 991]. Second, there is an increase in the concentration of glucose-6-phosphate, the allosteric activator of glycogen synthase [Villar-Palasi, C. and Guinovart, J. J. FASEB J. 1997, 11, 544]. Third, a kinase cascade beginning with the tyrosine kinase activity of the insulin receptor results in the phosphorylation and inactivation of GSK313, thereby preventing the deactivation of glycogen synthase [Cohen, P. Biochem. Soc. Trans. 1993, 21, 555; Yeaman, S. J. Biochem. Soc. Trans. 2001, 29, 537].

Because a significant decrease in the activity of glycogen synthase has been found in diabetic patients, and because of its key role in glucose utilization, the activation of the enzyme glycogen synthase holds therapeutic promise for the treatment of metabolic diseases such as type 2 diabetes and cardiovascular diseases. The only known allosteric activators of the enzyme are glucose-6-phosphate [Leloir, L. F. et al. Arch. Biochem. Biophys. 1959, 81, 508] and glucosamine-6-phosphate [Virkamaki, A. and Yki-Jarvinen, H. Diabetes 1999, 48, 1101].

The following biaryloxymethylarenecarboxylic acids are reported to be commercially available from Otava, Toronto, Canada, Akos Consulting & Solutions, Steinen, Germany or Princeton BioMolecular Research, Monmouth Junction, N.J.: 4-(biphenyl-4-yloxymethyl)-benzoic acid, 3-(biphenyl-4-yloxymethyl)-benzoic acid, [4-(biphenyl-4-yloxymethyl)-phenyl]-acetic acid, [4-(4'-methyl-biphenyl-4-yloxymethyl)-phenyl]-acetic acid, 4-(4'-methyl-biphenyl-4-yloxymethyl)-benzoic acid, 3-(3-bromo-biphenyl-4-yloxymethyl)-benzoic acid, [4-(3-bromo-biphenyl-4-yloxymethyl)-phenyl]-acetic acid, 2-(4'-methyl-biphenyl-4-yloxymethyl)-benzoic acid, 5-(biphenyl-4-yloxymethyl)-furan-2-carboxylic acid, 5-(4'-methyl-biphenyl-4-yloxymethyl)-furan-2-carboxylic acid, 5-(3-bromo-biphenyl-4-yloxymethyl)-furan-2-carboxylic acid, 4-(biphenyl-4-yloxymethyl)-5-methyl-furan-2-carboxylic acid, 5-methyl-4-(4'-methyl-biphenyl-4-yloxymethyl)-furan-2-carboxylic acid, 4-(3-bromo-biphenyl-4-yloxymethyl)-5-methyl-furan-2-carboxylic acid, 2-(biphenyl-4-yloxymethyl)-4-methyl-thiazole-5-carboxylic acid, [2-(biphenyl-4-yloxymethyl)-thiazol-4-yl]-acetic acid, [2-(4'-methyl-biphenyl-4-yloxymethyl)-thiazol-4-yl]-acetic acid and [5-(biphenyl-4-yloxymethyl)-[1,3,4]oxadiazol-2-yl]-acetic acid.

Some biaryloxymethylarenecarboxylic acids are known in the art. However, none of these known compounds have been associated with either the treatment of diseases mediated by the activation of the glycogen synthase enzyme or to any pharmaceutical composition for the treatment of diseases mediated by the activation of the glycogen synthase enzyme. Andersen, H. S. et al. WO 9740017 discloses the structure and synthetic route to 3-(biphenyl-4-yloxymethyl)-benzoic acid as an intermediate in the synthesis of SH2 inhibitors. Winkelmann, E. et al. DE 2842243 discloses 5-(biphenyl-4-yloxymethyl)-thiophene-2-carboxylic acid as a hypolipemic agent. Mueller, T. et al. DE 4142514 discloses 2-(biphenyl-3-yloxymethyl)-benzoic acid as a fungicide. Ghosh, S. S. et al. WO 2004058679 discloses biaryloxymethylarene acids as ligands of adenine nucleoside translocase. Van Zandt, M. C. WO 2008033455 discloses biphenyl and heteroarylphenyl derivatives as protein phosphatase-1B inhibitors.

Glycogen synthase activators and stimulators of glycogen production have been reported. Chu, C. A et al. US 20040266856 discloses biaryoxymethylarenecarboxylic acids as glycogen synthase activators. Chu, C.A. WO 2005000781 discloses biaryloxymethylarene carboxylic acids as activators of glycogen synthase. Yang, S-P. and Huang, Y. US 20050095219 discloses hyaluronic acid compounds that stimulate glycogen production. Gillespie, P. et al. WO 2005075468 discloses biaryoxymethylarene carboxylic acids as glycogen synthase activators. Gillespie, P. et al. WO 2006058648 discloses biaryoxymethylarene carboxylic acids as glycogen synthase activators. Bucala, R. et al. WO 2007044622 discloses macrophage migration inhibitory factor agonists that stimulate glycogen production.

SUMMARY OF THE INVENTION

The present invention is directed to compounds of the formula I:

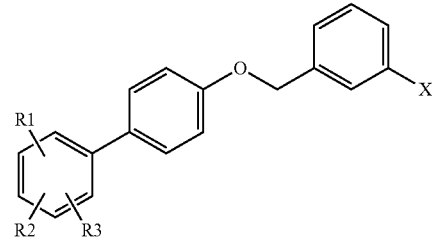

as well as pharmaceutically acceptable salts thereof, pharmaceutical compositions containing them and to methods of treating diseases and disorders. The compounds and compositions disclosed herein are glycogen synthase activators and are useful for the treatment of metabolic diseases and disorders, preferably diabetes mellitus, more preferably type II diabetes mellitus.

DETAILED DESCRIPTION OF THE INVENTION

In an embodiment of the present invention, provided is a compound of Formula (I):

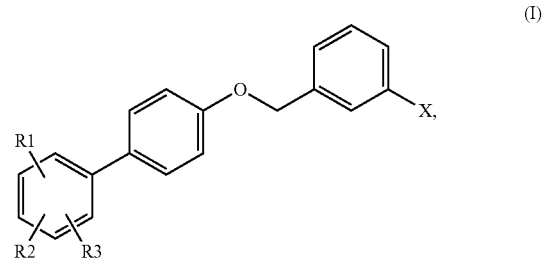

wherein:
R1, R2, R3, independently or each other, is hydrogen, halogen, lower alkyl or alkoxy;
X is —NR4R5, unsubstituted pyrollidine or pyrollidine substituted with acid;
R4 is hydrogen, lower alkyl or acyl moiety; and
R5 is an acyl moiety, —CH$_2$COOH, or —SO$_2$-lower alkyl unsubstituted or mono-, bi- or trisubstituted with halogen;
or a pharmaceutically acceptable salt thereof.

Preferably, R1, R2, R3, independently of each other, is hydrogen, halogen, lower alkyl or alkoxy; and X is —NR4R5.

Preferably, R1, R2, R3, independently of each other, is hydrogen, halogen, lower alkyl or alkoxy; and X is unsubstituted pyrollidine or pyrollidine substituted with acid.

Preferably, R4 is hydrogen, lower alkyl or acyl moiety; and R5 is an acyl moiety, —CH$_2$COOH, or —SO$_2$-lower alkyl unsubstituted or mono-, bi- or trisubstituted with halogen.

Preferably, R4 is an acyl moiety and R5 is an acyl moiety.
Preferably, R4 is hydrogen and R5 is an acyl moiety.

Preferably, R4 is hydrogen and R5 is —SO$_2$-lower alkyl unsubstituted or mono-, bi- or trisubstituted with halogen.

Preferably, X is —NR4R5.

Preferably, X is unsubstituted pyrollidine or pyrollidine substituted with an acid.

Preferably, X is unsubstituted pyrollidine.

Preferably, X is pyrollidine substituted with carboxylic acid or acetic acid.

Preferably, R1, R2, R3, independently of each other, is hydrogen, fluoro, chloro, methyl or methoxy.

Preferably, R1 is hydrogen or fluoro.

Preferably, R2 if fluoro.

Preferably, R3 is fluoro or methoxy.

Preferably, R4 is hydrogen or —C(O)CH$_3$.

Preferably, R4 is hydrogen.

Preferably, R5 is an acyl moiety.

Preferably, R5 is —C(O)(CH$_2$)$_2$COOH or —C(O)-cycloalkyl.

Preferably, R5 is —C(O)-cyclopentane, unsubstituted or substituted with —COOH.

Preferably, R5 is —CH$_2$COOH or —SO$_2$-lower alkyl unsubstituted or mono-, bi- or trisubstituted with halogen.

Preferably, R5 is —SO$_2$CH$_3$ or —SO$_2$CF$_3$.

Preferably, the compound according to formula (I) is:

N-[3-(2',4'-Difluoro-biphenyl-4-yloxymethyl)-phenyl]-succinamic acid;

(trans)-2-[3-(2',4'-Difluoro-biphenyl-4-yloxymethyl)-phenylcarbamoyl]-cyclopentanecarboxylic acid;

(1R,2R)-2-[3-(2',4'-Difluoro-biphenyl-4-yloxymethyl)-phenylcarbamoyl]-cyclopentanecarboxylic acid;

(1S,2S)-2-[3-(2',4'-Difluoro-biphenyl-4-yloxymethyl)-phenylcarbamoyl]-cyclopentanecarboxylic acid;

(1R,2S)-2-[3-(2',4'-Difluoro-biphenyl-4-yloxymethyl)-phenylcarbamoyl]-cyclopentanecarboxylic acid;

(1S,2R)-2-[3-(2',4'-Difluoro-biphenyl-4-yloxymethyl)-phenylcarbamoyl]-cyclopentanecarboxylic acid;

(S)-1-[3-(4',5'-Difluoro-2'-methoxy-biphenyl-4-yloxymethyl)-phenyl]-pyrrolidine-2-carboxylic acid;

{(S)-1-[3-(4',5'-Difluoro-2'-methoxy-biphenyl-4-yloxymethyl)-phenyl]-pyrrolidin-2-yl}-acetic acid;

{Acetyl-[3-(4',5'-difluoro-2'-methoxy-biphenyl-4-yloxymethyl)-phenyl]-amino}-acetic acid;

N-[3-(2',4',5'-Trifluoro-biphenyl-4-yloxymethyl)-phenyl]-methanesulfonamide;

N-[3-(4',5'-Difluoro-2'-methoxy-biphenyl-4-yloxymethyl)-phenyl]-methanesulfonamide;

C,C,C-Trifluoro-N-[3-(2',4',5'-trifluoro-biphenyl-4-yloxymethyl)-phenyl]methanesulfonamide; and N-[3-(4',5'-Difluoro-2'-methoxy-biphenyl-4-yloxymethyl)-phenyl]-C,C,C-trifluoromethanesulfonamide.

In another preferred embodiment, provided is a pharmaceutical composition, comprising a therapeutically effective amount of a compound according to formula (I) and a pharmaceutically acceptable carrier and/or adjuvant.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents with the understanding that said substituents are not, in turn, substituted further unless indicated otherwise in the Examples or claims below. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, pyranyl, morpholinyl, thiomorpholinyl, piperazinyl, piperidinyl, pyrrolidinyl, tetrahydropyranyl, tetrahydrofuranyl, 1,3-dioxanyl, dioxidoisothiazolidine and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms, most preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

As used herein, the term "acyl" means an optionally substituted alkyl, cycloalkyl, heterocyclic, aryl or heteroaryl group bound via a carbonyl group and includes groups such as acetyl, —C(O)-lower alkyl (unsubstituted or substituted with, for example, —COOH), —C(O)-cyclopentane (unsubstituted or substituted with, for example, —COOH), and the like.

The term "aryl" refers to an aromatic mono- or polycarbocyclic radical of 6 to 12 carbon atoms having at least one aromatic ring. Examples of such groups include, but are not limited to, phenyl and napthyl.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. The heteroaryl group may be substituted independently with one, two, or three substituents, with the understanding that said substituents are not, in turn, substituted further unless indicated otherwise in the Examples or claims below.

As used herein, the term "alkoxy" means alkyl-O—; and "alkoyl" means alkyl-CO—. Alkoxy substituent groups or alkoxy-containing substituent groups may be substituted by, for example, one or more alkyl groups with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula (I) in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, NJ; Teledyne Isco, Lincoln, Nebr.; VWR International, Bridgeport, NJ; Varian Inc., Palo Alto, Calif., and Multigram II Mettler Toledo Instrument Newark, Del. Biotage, ISCO and Analogix columns are pre-packed silica gel columns used in standard chromatography.

Definitions as used herein include:
GS is glycogen synthase,
THF is tetrahydrofuran,
DMF is N,N-dimethylformamide,
DMA is N,N-dimethylacetamide,
DMSO is dimethylsulfoxide,
DCM is dichloromethane,
DME is dimethoxyethane,
MeOH is methanol,
EtOH is ethanol,
DIAD is diisopropyl azodicarboxylate,
DMAP is N,N-dimethylamino-pyridine,
HATU is O-(azabenzotriazol-1-yl)-N,N,N',N'-tetramethyluronium hexafluorophosphate,
BOP is (benzotriazol-1-yloxy)tris(dimethylamino)phosphonium hexafluorophosphate,
TFA is 1,1,1-trifluoroacetic acid,
DIPEA is diisopropylethylamine,
Boc is tert-butyloxycarbonyl,
EDC.HCl is N-(3-dimethylaminopropyl)-N'-ethylcarbodiimide hydrochloride,
Brine is saturated aqueous sodium chloride solution,
SFC is supercritical fluid chromatography,
TLC is thin layer chromatography, RP HPLC is reversed phase high performance liquid chromatography,
HR-MS is high resolution mass spectrometry,
LC-MS is liquid chromatographic mass spectrometry, and
RT is room or ambient temperature.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific examples listed in the later section.

The preparation of substituted biphenylphenols is described in Scheme 1, below. Commercially available phenylboronic acid (i) can be coupled with 4-halo-phenol (ii) under palladium catalysis conditions to form the bi-aryl-phenol (iii), where R1, R2 and R3 can be fluoro, chloro, methyl or methoxy groups and halo may be iodo or bromo. Alternatively, the required biphenylphenol (iii) can also be prepared through the coupling of 4-hydroxy-arylboronic acid (v) with the corresponding arylbromide (iv) under palladium catalysis conditions. Non-commercially available arylbromides (iv) can be prepared through aromatic bromination of vi.

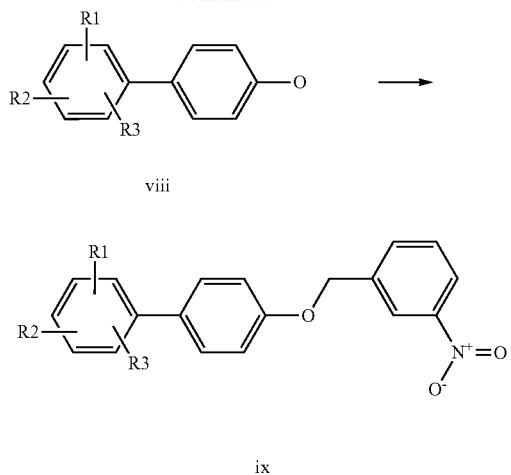

As shown in Scheme 3, m-N-Boc-benzyl alcohol (x) can be reacted under Mitsunobu conditions to give m-N-Boc-pro- Scheme 1

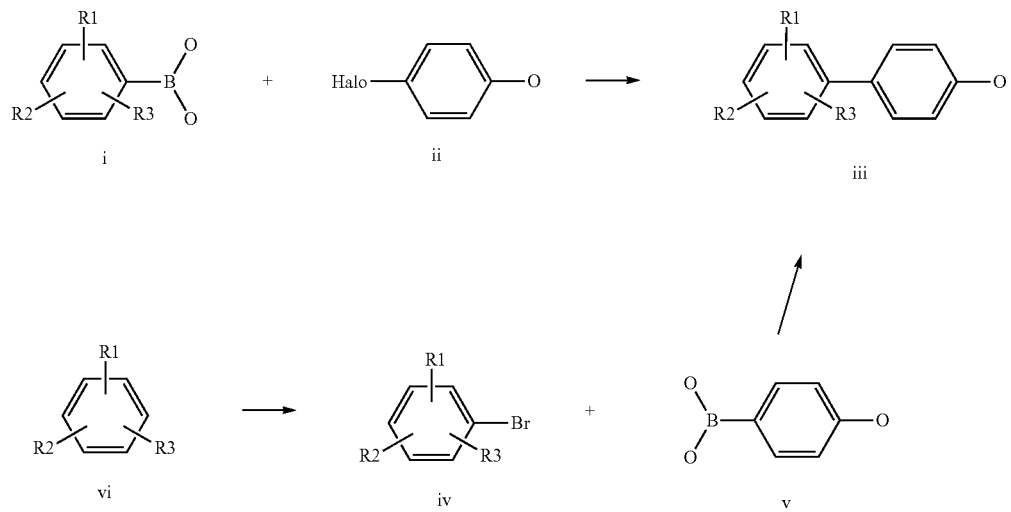

The preparation of substituted m-nitro-benzyl ethers (xi) is shown in Scheme 2. m-Nitro-benzyl bromide (vii) can be treated with substituted-biaryphenols under basic conditions, such as potassium carbonate, to give m-nitro-benzyl ethers ix, where R1, R2 and R3 can be fluoro, chloro, methyl or methoxy groups.

tected benzyl ethers (xi), where R1, R2 and R3 can be fluoro, chloro, methyl or methoxy groups. Alternatively, ix may be prepared under basic conditions from vii and viii using lithium bis(trimethylsilyl)amide.

Scheme 2

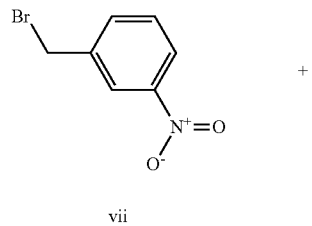

vii

Scheme 3

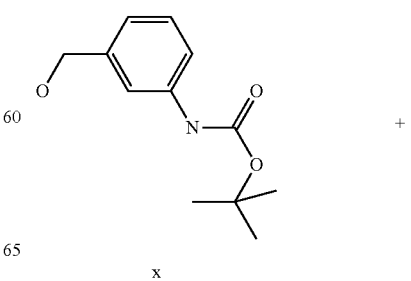

x

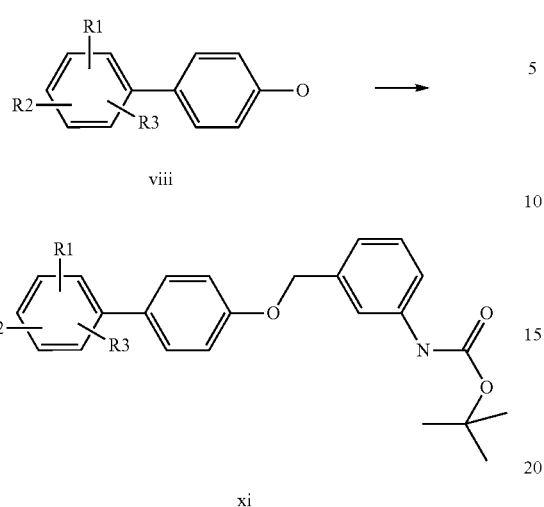

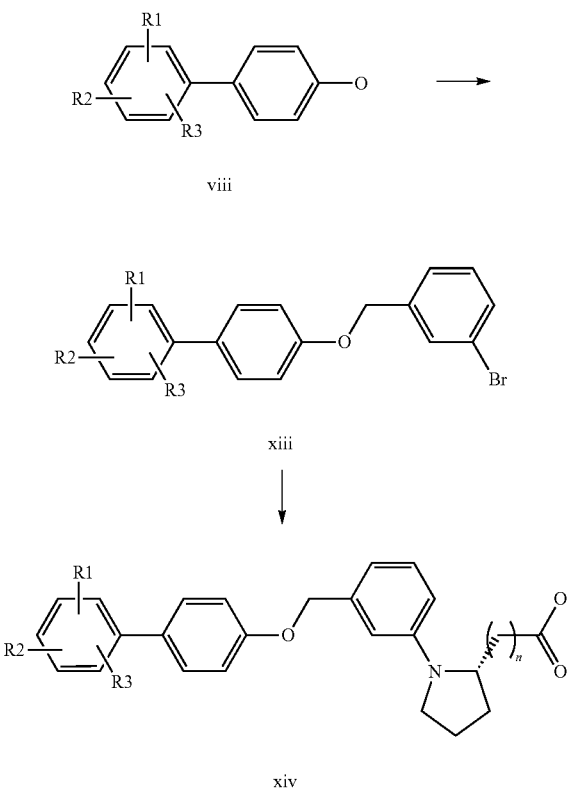

As shown in Scheme 4, m-bromo-benzyl bromide (xii) can be treated with substituted-biaryphenols (viii) under basic conditions, such as potassium carbonate, to give m-bromo-benzyl ethers xiii, where R1, R2 and R3 can be fluoro, chloro, methyl or methoxy groups. m-Bromo-benzyl ethers xiii may be heated with copper(I) iodide, sodium iodide, cesium carbonate and substituted pyrrolidines to give N-phenyl-pyrrolidines xiv, where R1, R2 and R3 can be fluoro, chloro, methyl or methoxy groups.

Scheme 4

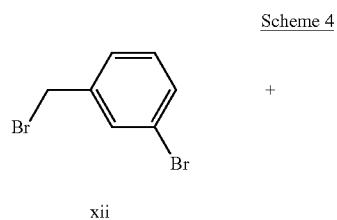

As shown in Scheme 5, aryl amines xvi may be formed from reduction of nitro-aryls, ix, by conditions such as catalytic hydrogenation or metal-based reduction, or by deprotection of N-Boc-protected intermediates, xi, under acidic conditions. Intermediate amines, xvi, can be acylated under a variety of conditions to yield acids xvii, where R1, R2 and R3 can be fluoro, chloro, methyl or methoxy groups. Alternatively, acids xv maybe prepared from xvi by stepwise treatment with bromo-acetic acid ethyl ester, acetyl chloride and lithium hydroxide, where R1, R2 and R3 can be fluoro, chloro, methyl or methoxy groups.

Scheme 5

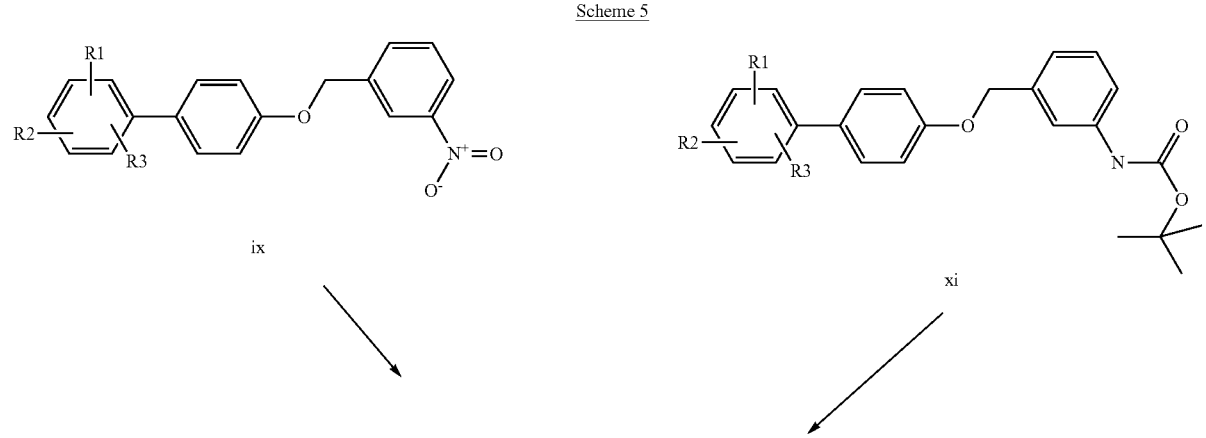

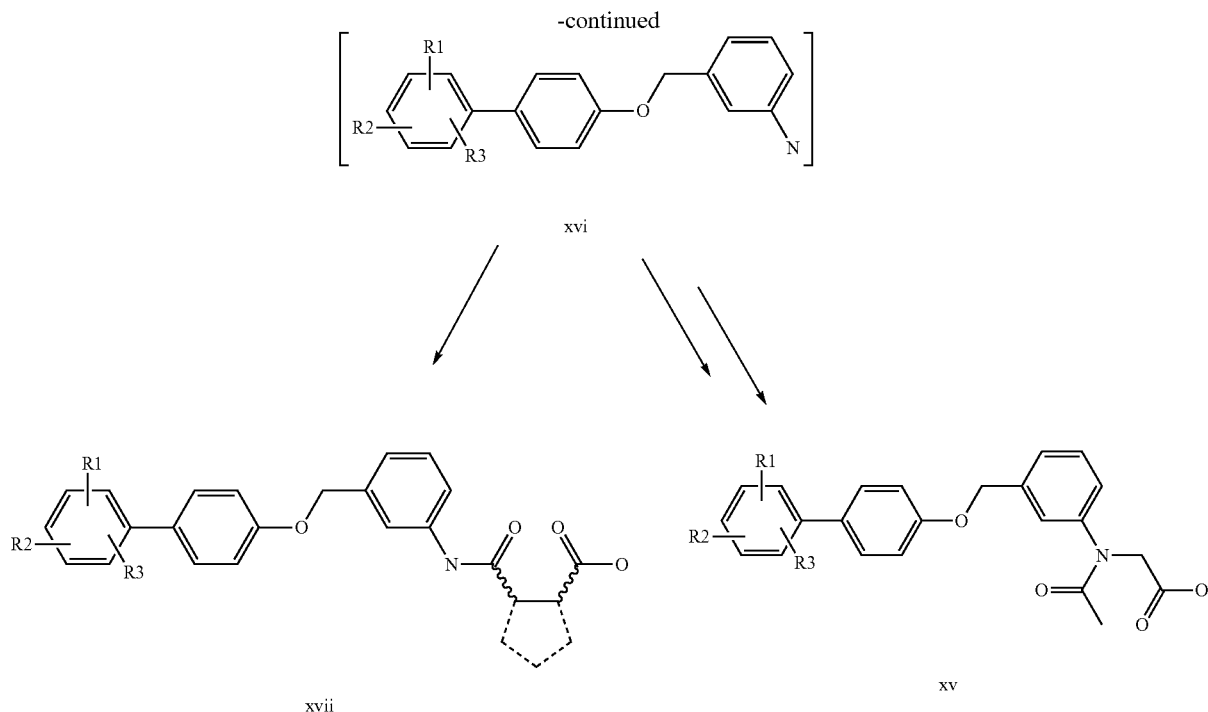

Sulfonamides xviii may be prepared as shown in Scheme 6 by reduction of nitro-aryls ix and sulfonylation of intermediate amines xvii, where R1, R2 and R3 can be fluoro, chloro, methyl or methoxy groups.

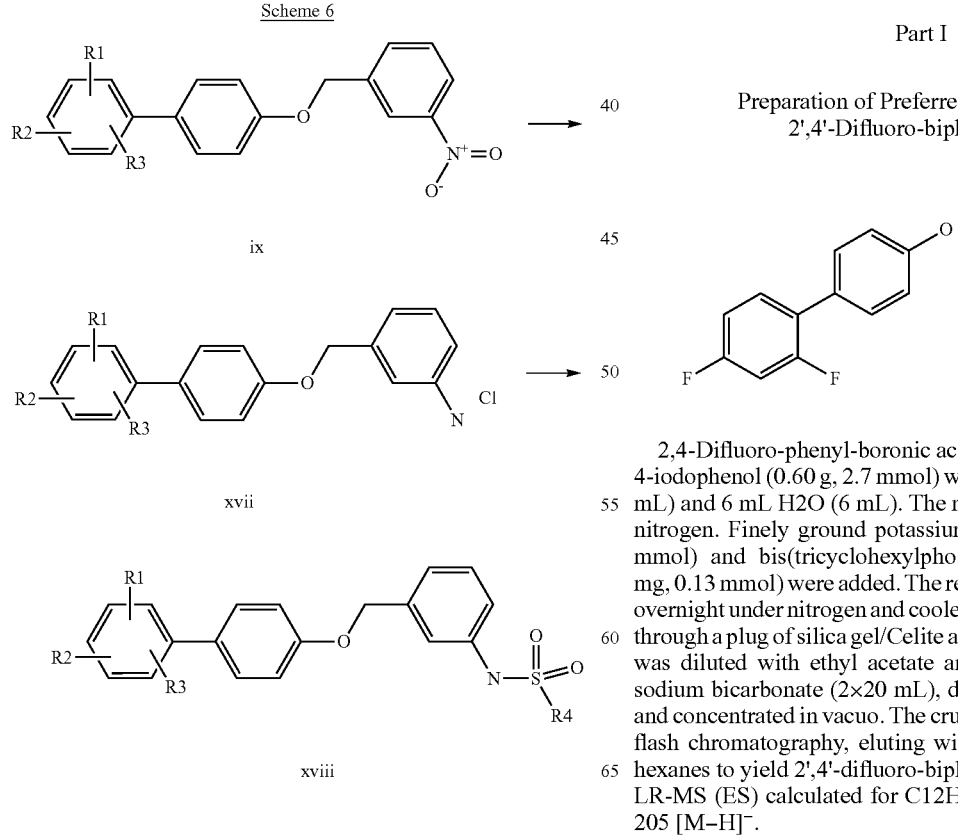

The invention will now be further described in the Examples below, which are intended as an illustration only and do not limit the scope of the invention.

EXAMPLES

Part I

Preparation of Preferred Intermediates
2',4'-Difluoro-biphenyl-4-ol 2,4-Difluoro-phenyl-boronic acid (1.29 g, 8.18 mmol) and 4-iodophenol (0.60 g, 2.7 mmol) were suspended in DMF (60 mL) and 6 mL H2O (6 mL). The mixture was degassed with nitrogen. Finely ground potassium carbonate (1.13 g, 8.18 mmol) and bis(tricyclohexylphosphine) palladium(0) (91 mg, 0.13 mmol) were added. The reaction was stirred at reflux overnight under nitrogen and cooled. The mixture was filtered through a plug of silica gel/Celite and evaporated. The residue was diluted with ethyl acetate and washed with saturated sodium bicarbonate (2×20 mL), dried over MgSO4, filtered and concentrated in vacuo. The crude product was purified by flash chromatography, eluting with 0-25% ethyl acetate in hexanes to yield 2',4'-difluoro-biphenyl-4-ol (0.61 g, 100%). LR-MS (ES) calculated for C12H8F2O, 206.19; found m/z 205 [M−H]−.

4',5'-Difluoro-2'-methoxy-biphenyl-4-ol

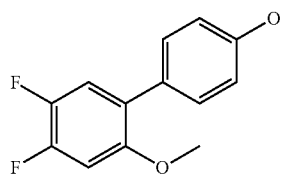

4,5-Difluoro-2-methoxyphenyl-boronic acid (8.8 g, 46.82 mmol) and 4-iodophenol (6.86 g, 31.21 mmol) were suspended in 165 ml of DMF. H2O (40 mL) was added and the mixture was degassed with argon. Finely ground potassium carbonate (13 g, 93.63 mmol) and tetrakis(triphenylphosphine) palladium(0) (1.5 g, 1.29 mmol) were added. The reaction was stirred at 80-85° C. for 1 hr under argon and cooled. The mixture was diluted with ethyl acetate and water. The organic layer was washed with brine, dried and solvents were evaporated. The crude product was purified by flash chromatography, eluting with 0-8% ethyl acetate in hexanes to yield 4',5'-difluoro-2'-methoxy-biphenyl-4-ol (6.58 g, 89.3%). LR-MS (ES) calculated for C13H10F2O, 236.22; found m/z 235 [M–H]⁻.

2',4',5'-Trifluoro-biphenyl-4-ol

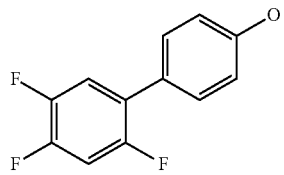

A mixture of 2,4,5-trifluorophenylboronic acid (43.8 g, 249.2 mmol), 4-iodophenol (50 g, 226.5 mmol), potassium carbonate (78 g, 556.3 mmol), Pd(dppf)Cl₂ methylene chloride complex (5.5 g, 6.8 mmol), DMF (150 mL), and water (38 mL) was degassed, purged with nitrogen, and heated at 50° C. overnight. The mixture was then diluted with EtOAc and water, acidified with conc. HCl under cooling with ice-water bath, stirred with charcoal, and filtered through Celite. The organic layer was separated, washed with water and brine, dried over sodium sulfate, filtered, and evaporated to afford a deep red oily crude product. The crude product in EtOAc was passed through silica gel to give 2',4',5'-trifluoro-biphenyl-4-ol as a light brown solid (38 g, 75%). LC-MS (ES) calculated for C12H7F3O, 224.18; found m/z 224 [M+H].

2,4-Difluoro-4'-(3-nitro-benzyloxy)-biphenyl

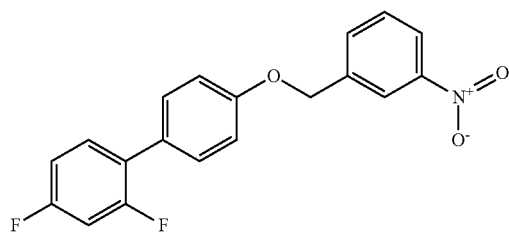

1-Bromomethyl-3-nitro-benzene (110 mg, 0.508 mmol), 2',4'-difluoro-biphenyl-4-ol (110 mg, 0.533 mmol), and dried, finely ground potassium carbonate (74 mg, 0.533 mmol) in 10 mL acetone were refluxed under argon for 20 hrs. The reaction mixture was cooled, filtered, concentrated and re-dissolved in ethyl acetate. The ethyl acetate solution was washed with saturated NaHCO₃, dried over MgSO₄, filtered and evaporated in vacuo. The crude product was purified by flash chromatography with a gradient of 0-20% ethyl acetate in hexanes to yield 0.11 g (63%) of 2,4-difluoro-4'-(3-nitro-benzyloxy)-biphenyl. LC-MS (ES) calculated for C19H13F2NO3, 341.32; found m/z 340.3 [M–H]⁻.

4,5-Difluoro-2-methoxy-4'-(3-nitro-benzyloxy)-biphenyl

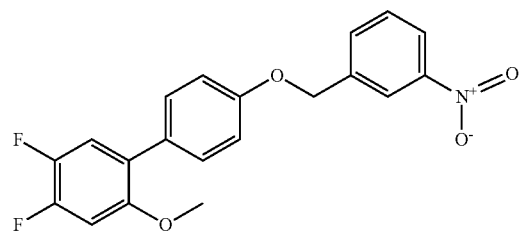

1-Bromomethyl-3-nitro-benzene (455 mg, 2.11 mmol), 4',5'-difluoro-2'-methoxy-biphenyl-4-ol (0.5 g, 2.11 mmol), and dried, finely ground potassium carbonate (363 mg, 2.63 mmol) in 30 mL acetone were refluxed under argon for 16 hrs similar to 2,4-difluoro-4'-(3-nitro-benzyloxy)-biphenyl above. The crude product was purified by trituration with 5% ethyl acetate in hexanes to yield 0.31 g (38%) of 4,5-difluoro-2-methoxy-4'-(3-nitro-benzyloxy)-biphenyl. LC-MS (ES) calculated for C20H15F2NO4, 371.34; found m/z 370 [M–H]⁻.

2,4,5-Trifluoro-4'-(3-nitro-benzyloxy)-biphenyl

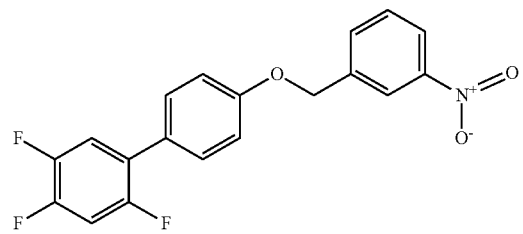

1-Bromomethyl-3-nitro-benzene (0.9 g, 4.2 mmol), 2',4',5'-trifluoro-biphenyl-4-ol (1.15 g, 4.2 mmol), and dried, finely ground potassium carbonate (725 mg, 5.25 mmol) in 40 mL acetone were refluxed under argon for 19 hrs similar to 2,4-difluoro-4'-(3-nitro-benzyloxy)-biphenyl above. The crude product was purified by flash chromatography with 0-6% ethyl acetate in hexanes to yield 0.71 g (47%) of 2,4,5-trifluoro-4'-(3-nitro-benzyloxy)-biphenyl. LC-MS (ES) calculated for C19H12F3NO3, 359.31; found m/z 358 [M–H]⁻.

[3-(2',4'-Difluoro-biphenyl-4-yloxymethyl)-phenyl]-carbamic acid tert-butyl ester

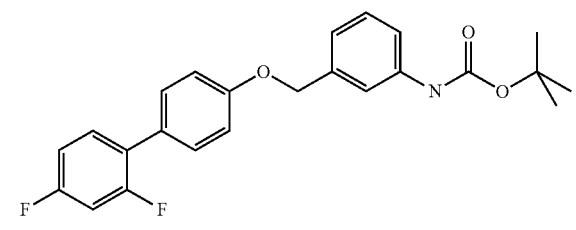

To 10 mL of dry CH2Cl2 under argon, in an ice bath, was added 2',4'-difluoro-biphenyl-4-ol (206 mg, 1.0 mmol) and triphenylphosphine resin (1.1 meq/g, 1.36 g, 1.5 mmol). The mixture was stirred for 20 min and DIAD (295 uL, 1.5 mmol) was added. The reaction was stirred an additional 5 min at ice bath temperature and [3-(2',4'-difluoro-biphenyl-4-yloxymethyl)-carbamic acid tert-butyl ester (223 mg, 1.0 mmol) and triethylamine (209 uL, 1.5 mmol) were added. The mixture was stirred at ice bath temperature for 20 min and allowed to warm slowly to RT and stirred overnight. The reaction mixture was filtered, concentrated and purified by flash chromatography with a gradient of 0-10% ethyl acetate in hexanes to yield 235.4 mg (57%) of [3-(2',4'-difluoro-biphenyl-4-yloxymethyl)-phenyl]-carbamic acid tert-butyl ester. $^1$H-NMR (CDCl$_3$) δ ppm 1.52 (s, 2H), 6.51 (br. S, 1H), 6.82-6.98 (m, 2H), 7.03 (d, J=8.7 Hz, 2H), 7.08-7.17 (m, 1H), 7.28-7.39 (m, 3H), 7.42 (d, j=8.7 Hz, 2H), 7.50 (s, 1H).

rac-(trans)-Cyclopentane-1,2-dicarboxylic acid mono-(2,4-dimethoxy-benzyl)ester

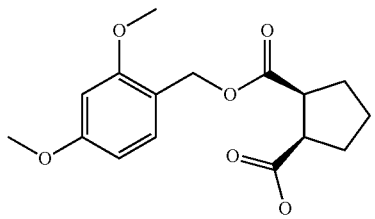

To a solution of (trans)-cyclopentane-1,2-dicarboxylic acid (1.90 g, 12 mmol), 2,4-dimethoxy-benzyl alcohol (2.02 g, 12 mmol), DMAP (73 mg, 0.6 mmol) in DMF (30 mL), chilled in an ice bath, was added EDC.HCl (2.53 g, 13.2 mmol) in two portions. The mixture was stirred at ice bath temperature for 15 min and warmed to RT for 4 hrs. The reaction mixture was diluted with H2O (100 mL) and saturated NaHCO3 (40 mL). The aqueous mixture was extracted with EtOAC (3×30 mL), acidified to pH 3 with saturated KHSO4 and extracted with EtOAc (3×30 mL). The combined organic layers were washed with H2O (2×25 mL), saturated NaCl (25 mL), dried over MgSO4, filtered and evaporated. The crude material was re-dissolved in CHCl3 and eluted through a silica gel plug with CHCl3 (100 mL) and then EtOAc (100 mL). The EtOAc fraction was evaporated and pumped to a clear oil, 2.6 g (70%), and used without further purification.

Part II

Preparation of Preferred Embodiments of the Invention

Example 1

N-[3-(2',4'-Difluoro-biphenyl-4-yloxymethyl)-phenyl]-succinamic acid

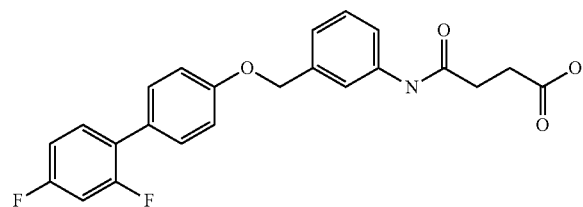

A mixture of 2,4-difluoro-4'-(3-nitro-benzyloxy)-biphenyl (28 mg, 0.082 mmol), succinic anhydride (8.2 mg, 0.083 mmol) and 10% Pd/C (4.4 mg) in THF (3 mL) was hydrogenated at 45 psi for 4 hrs. The reaction mixture was filtered and evaporated. The crude product was purified by flash chromatography with a 0-50% gradient of ethyl acetate in hexanes to yield 7 mg (20.7%) of N-[3-(2',4'-difluoro-biphenyl-4-yloxymethyl)-phenyl]-succinamic acid as a solid. LC-MS (ES) calculated for C23H19F2NO4, 411.41; found m/z 410.2 [M–H]$^-$.

Example 2

(trans)-2-[3-(2',4'-Difluoro-biphenyl-4-yloxymethyl)-phenylcarbamoyl]-cyclopentanecarboxylic acid

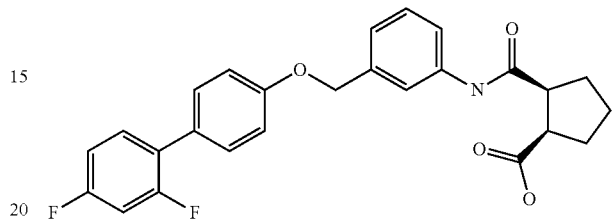

A mixture of 2,4-difluoro-4'-(3-nitro-benzyloxy)-biphenyl (26.3 mg, 0.077 mmol) and 10% Pd/C (5.3 mg) in EtOH (3 mL) containing 2 drops 2N HCl was hydrogenated at 50 psi for 2 hrs. The reaction mixture was filtered and evaporated. The crude product was dissolved in DMF (1 mL) with rac-(trans)-cyclopentane-1,2-dicarboxylic acid monobenzyl ester (19.5 mg, 0.77 mmol), triethylamine (32 uL, 0.231 mmol) and BOP (33 mg, 0.077 mmol). The mixture was stirred for 1 hr at RT. DMAP (1 mg) was added and stirring continued overnight. The reaction mixture was diluted with EtOAc (20 mL), washed with 2.5% KHSO4 (3×10 mL), 50% saturated NaHCO3 (10 mL), saturated NaCl (10 mL), dried over MgSO4, filtered and evaporated. The crude ester was purified by flash chromatography with a 0-20% gradient of ethyl acetate in hexanes to yield 18.3 mg of (trans)-2-[3-(2',4'-difluoro-biphenyl-4-yloxymethyl)-phenylcarbamoyl]-cyclopentanecarboxylic acid benzyl ester as a clear oil. This material was dissolved in EtOH (3 mL) with 10% Pd/C (4 mg) and hydrogenated at 50 psi for 1 hr. The reaction mixture was filtered through Celite and evaporated to give (trans)-2-[3-(2',4'-difluoro-biphenyl-4-yloxymethyl)-phenylcarbamoyl]-cyclopentanecarboxylic acid as a white solid (16.4 mg, 47%). LC-MS (ES) calculated for C26H23F2NO4, 451.47; found m/z 450.2 [M–H]$^-$.

Example 3

(1R,2R)-2-[3-(2',4'-Difluoro-biphenyl-4-yloxymethyl)-phenylcarbamoyl]-cyclopentanecarboxylic acid

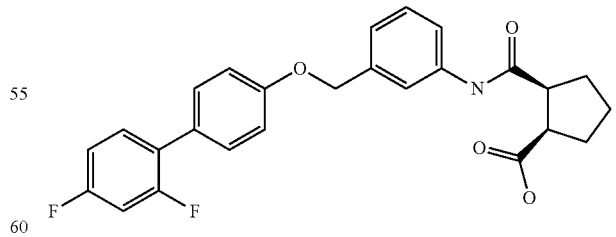

[3-(2',4'-Difluoro-biphenyl-4-yloxymethyl)-phenyl]-carbamic acid tert-butyl ester (117 mg, 0.284 mmol) was stirred in 5 mL EtOAc (saturated with HCl) at RT for 45 min. The mixture was evaporated, re-evaporated from EtOAc and pumped under high vacuum to give a solid. The crude product was dissolved in 50% CH2Cl2/DMF (1.5 mL). To this solution was added triethylamine (119 uL, 0.853 mmol) and rac- (trans)-cyclopentane-1,2-dicarboxylic acid mono-(2,4-dimethoxy-benzyl)ester (92 mg, 0.298 mmol). This solution was stirred for 5 minutes as HATU (114, 0.298 mmol) was added and then let stir at RT overnight. The reaction mixture was diluted with EtOAc (25 mL), washed with 2.5% KHSO4 (2×10 mL), H2O (2×5 mL), saturated NaHCO3 (2×10 mL), saturated NaCl (10 mL) and evaporated to give 220 mg of crude product.

The crude benzyl ester was dissolved in 50% TFA/$CH_2Cl_2$ (10 mL) and stirred at RT for 30 min and then evaporated. The crude product was purified by flash chromatography with a 0-60% gradient of ethyl acetate/MeOH/AcOH (95:5:1) in hexanes to yield 66 mg of rac-(trans)-2-[3-(2',4'-difluoro-biphenyl-4-yloxymethyl)-phenylcarbamoyl]-cyclopentanecarboxylic acid as a white solid. LC-MS (ES) calculated for C26H23F2NO4, 451.47; found m/z 450.1 [M−H]⁻.

Racemic (trans)-2-[3-(2',4'-difluoro-biphenyl-4-yloxymethyl)-phenylcarbamoyl]-cyclopentanecarboxylic acid was separated by preparative SFC in multiple runs in on a Diacel OJ column (30% MeOH, 30° C., 70 mL/min and 100 bar $CO_2$). The first band to elute was evaporated to give 22.0 mg (17%) of (1R,2R)-2-[3-(2',4'-difluoro-biphenyl-4-yloxymethyl)-phenylcarbamoyl]-cyclopentanecarboxylic acid as a white solid. LC-MS (ES) calculated for C26H23F2NO4, 451.47; found m/z 450.3 [M−H]⁻.

Example 4

(1S,2S)-2-[3-(2',4'-Difluoro-biphenyl-4-yloxymethyl)-phenylcarbamoyl]-cyclopentanecarboxylic acid

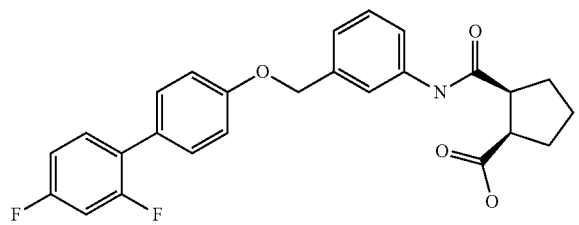

The second band to elute from the above SFC purification of rac-(trans)-2-[3-(2',4'-difluoro-biphenyl-4-yloxymethyl)-phenylcarbamoyl]-cyclopentanecarboxylic acid was evaporated to give 28.0 mg (21.8%) of (1S,2S)-2-[3-(2',4'-difluoro-biphenyl-4-yloxymethyl)-phenylcarbamoyl]-cyclopentanecarboxylic acid as a white solid. LC-MS (ES) calculated for C26H23F2NO4, 451.47; found m/z 450.3 [M−H]⁻.

Example 5

(1R,2S)-2-[3-(2',4'-Difluoro-biphenyl-4-yloxymethyl)-phenylcarbamoyl]-cyclopentanecarboxylic acid

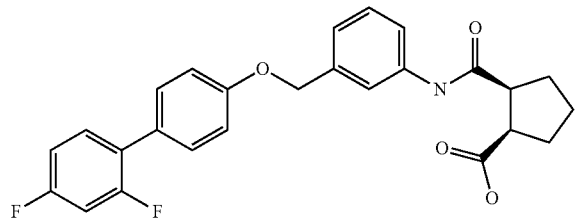

[3-(2',4'-Difluoro-biphenyl-4-yloxymethyl)-phenyl]-carbamic acid tert-butyl ester (111 mg, 0.269 mmol) was stirred in 5 mL EtOAc (saturated with HCl) at RT for 45 min. The mixture was evaporated, re-evaporated from EtOAc and pumped under high vacuum to give a solid. The crude product was dissolved in DMF (2 mL). To this solution, chilled in an ice bath, was added triethylamine (150 uL, 1.08 mmol), (cis)-cyclopentane-1,2-dicarboxylic acid (64 mg, 0.404 mmol) and HATU (154, 0.404 mmol) was added and then let stir at RT for 30 min. The reaction mixture was diluted with EtOAc (25 mL), washed with 1N HCl (10 mL), H2O (10 mL), saturated NaCl (10 mL), dried over MgSO4, filtered and evaporated to give a white solid. The crude product was purified by flash chromatography with a 0-55% gradient of ethyl acetate/MeOH/AcOH (95:5:1) in hexanes to yield 64.8 mg of rac-(cis)-2-[3-(2',4'-difluoro-biphenyl-4-yloxymethyl)-phenylcarbamoyl]-cyclopentanecarboxylic acid as a white solid.

Racemic (cis)-2-[3-(2',4'-difluoro-biphenyl-4-yloxymethyl)-phenylcarbamoyl]-cyclopentanecarboxylic acid was separated by preparative SFC in multiple runs in on a Diacel OJ column (40% MeOH, 30° C., 70 mL/min and 100 bar $CO_2$). The first band to elute was evaporated to give 30.2 mg (24.8%) of (1R,2S)-2-[3-(2',4'-difluoro-biphenyl-4-yloxymethyl)-phenylcarbamoyl]-cyclopentanecarboxylic acid as a white solid. LC-MS (ES) calculated for C26H23F2NO4, 451.47; found m/z 450.2 [M−H]⁻.

Example 6

(1S,2R)-2-[3-(2',4'-Difluoro-biphenyl-4-yloxymethyl)-phenylcarbamoyl]-cyclopentanecarboxylic acid

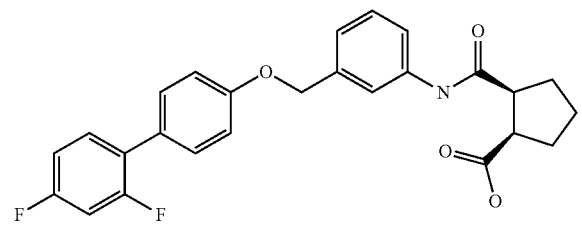

The second band to elute from the above SFC purification of rac-(cis)-2-[3-(2',4'-difluoro-biphenyl-4-yloxymethyl)-phenylcarbamoyl]-cyclopentanecarboxylic acid was evaporated to give 31.0 mg (25.5%) of (1S,2R)-2-[3-(2',4'-difluoro-biphenyl-4-yloxymethyl)-phenylcarbamoyl]-cyclopentanecarboxylic acid as a white solid. LC-MS (ES) calculated for C26H23F2NO4, 451.47; found m/z 450.3 [M−H]⁻.

Example 7

(S)-1-[3-(4',5'-Difluoro-2'-methoxy-biphenyl-4-yloxymethyl)-phenyl]-pyrrolidine-2-carboxylic acid

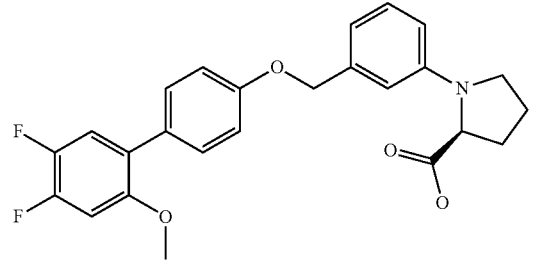

To a mixture of DMF (5 ml), 1-bromo-3-bromomethyl-benzene (0.50 g, 2.0 mmol) and potassium carbonate (0.55 g, 4.0 mmol) was added 4',5'-difluoro-2'-methoxy-biphenyl-4- ol (0.48 g, 2.0 mmol). The reaction was sealed and heated at 80° C. for 3 hr then cooled to RT overnight. The mixture was diluted with ethyl acetate (200 mL), washed with water (200 ml) and brine (saturated NaCl), dried over sodium sulfate and concentrated as a clear, viscous oil (0.8 g, 98%). The product, 4'-(3-bromo-benzyloxy)-4,5-difluoro-2-methoxy-biphenyl, contained DMF (10 mole %) and was used without further purification. LC-MS (ES) calculated for C20H15BrF2O2, 404.02; found m/z 404 [M+H]$^+$.

To a vial containing copper(I) iodide (10 mg, 0.050 mmol), sodium iodide (30 mg, 0.2 mmol), cesium carbonate (114 mg, 0.35 mmol) and (S)-pyrrolidine-2-carboxylic acid (14 mg, 0.12 mmol) was added an aliquot of a stock solution of 4'-(3-bromo-benzyloxy)-4,5-difluoro-2-methoxy-biphenyl (1 ml of 0.1M in DMSO). The vial was sealed and heated to 100° C. for 15 hr. The reaction was filtered through Celite and purified by HPLC with increasing concentration of acetonitrile in water with 0.1% trifluoroacetic acid, yielding the product, (S)-1-[3-(4',5'-difluoro-2'-methoxy-biphenyl-4-yloxymethyl)-phenyl]-pyrrolidine-2-carboxylic acid as an off white solid (11 mg, 25%). LC-MS (ES) calculated for C25H23F2NO4, 439.16; found m/z 440 [M+H]$^+$.

Example 8

{(S)-1-[3-(4',5'-Difluoro-2'-methoxy-biphenyl-4-yloxymethyl)-phenyl]-pyrrolidin-2-yl}-acetic acid

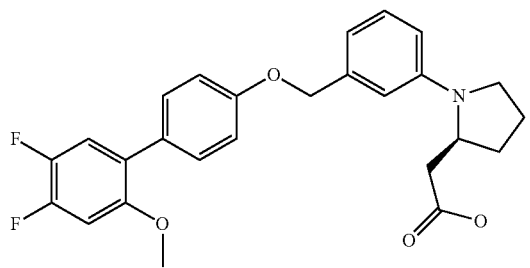

4'-(3-Bromo-benzyloxy)-4,5-difluoro-2-methoxy-biphenyl (142 mg, 0.35 mmol), copper(I) iodide (40 mg, 0.21 mmol), sodium iodide (105 mg, 0.70 mmol), cesium carbonate (687 mg, 2.1 mmol) and (S)-pyrrolidin-2-yl-acetic acid (106 mg, 0.78 mmol) and DMSO (0.35 ml) were reacted as above to yield 73 mg of {(S)-1-[3-(4',5'-difluoro-2'-methoxy-biphenyl-4-yloxymethyl)-phenyl]-pyrrolidin-2-yl}-acetic acid as a white solid. LC-MS (ES) calculated for C26H25F2NO4, 453.18; found m/z 454 [M+H]$^+$.

Example 9

{Acetyl-[3-(4',5'-difluoro-2'-methoxy-biphenyl-4-yloxymethyl)-phenyl]-amino}-acetic acid

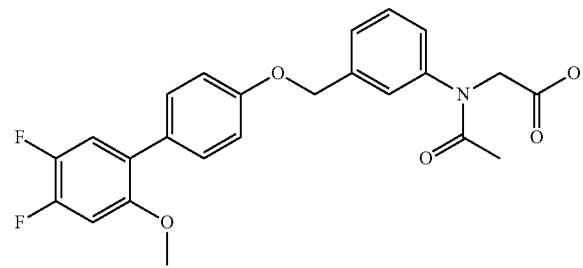

To a mixture of DMF (5 ml), 1-bromomethyl-3-nitro-benzene (0.92 g, 4.2 mmol), and 4',5'-difluoro-2'-methoxy-biphenyl-4-ol (1 g, 4.2 mmol) was added lithium bis(trimethylsilyl)amide (1M in THF, 4.4 ml). The reaction was stirred at room temperature overnight and was then diluted with ethyl acetate (200 mL), washed with water (200 mL), aqueous ammonium chloride (10%, 200 mL) and brine, dried over magnesium sulfate and concentrated to yield 4,5-difluoro-2-methoxy-4'-(3-nitro-benzyloxy)-biphenyl as yellow solid (1.5 g, 95%). LC-MS (ES) calculated for C20H15F2NO4, 371.1; found m/z 370 [M–H]$^-$.

To a flask containing 4,5-difluoro-2-methoxy-4'-(3-nitro-benzyloxy)-biphenyl (1.49 g, 4.0 mmol) was added ethanol (40 ml), zinc (2.5 g, 40 mmol) and ammonium chloride (3.2 g, 60.2 mmol). Additional solvent was added over time, ethanol (30 mL at 15 min) and ethyl acetate (10 mL at 45 min). After 1 hr the reaction was filtered through Celite, concentrated, diluted with ethyl acetate (100 mL), washed with saturated aqueous sodium bicarbonate (200 mL) and brine (100 mL), dried over magnesium sulfate, concentrated and dried from hexanes/methylene chloride mixtures to yield 3-(4',5'-difluoro-2'-methoxy-biphenyl-4-yloxymethyl)-phenylamine as a yellow oil (1.4 g, 100%). LC-MS (ES) calculated for C20H17F2NO2, 341.12; found m/z 342 [M+H]$^+$.

To a vial containing 3-(4',5'-difluoro-2'-methoxy-biphenyl-4-yloxymethyl)-phenylamine (0.35 g, 1.0 mmol) dissolved in acetonitrile (1 mL) was added bromo-acetic acid ethyl ester (0.113 ml, 1.0 mmol) and potassium carbonate (167 mg, 1.2 mmol) and additional acetonitrile (5 mL). The vial was sealed and heated to 80° C. overnight. The reaction was partitioned between ethyl acetate (200 mL) and aqueous HCl (0.1 M, 200 mL). The organic layer was separated and the aqueous layer extracted with ethyl acetate (200 mL). The organic layers were washed with brine (100 mL), combined, dried over magnesium sulfate, concentrated, dissolved in a minimal amount of dichloromethane and purified by flash chromatography with a 0-30% ethyl acetate in hexanes gradient to yield [3-(4',5'-difluoro-2'-methoxy-biphenyl-4-yloxymethyl)-phenylamino]-acetic acid ethyl ester as a clear semisolid (190 mg, 44%). LC-MS (ES) calculated for C24H23F2NO4, 427.16; found m/z 428 [M+H]$^+$.

To a vial containing [3-(4',5'-difluoro-2'-methoxy-biphenyl-4-yloxymethyl)-phenylamino]-acetic acid ethyl ester (47 mg, 0.11 mmol) dissolved in dimethylformide (1 mL) was added lithium bis(trimethylsilyl)amide (1 M in THF, 0.13 mL, 0.13 mmol), diisopropylethyl amine (0.238 mL, 1.3 mmol) and acetyl chloride. The reaction was stirred at room temperature overnight. Reaction was filtered and purified by HPLC with increasing concentration of acetonitrile in water with 0.1% trifluoroacetic acid to yield {acetyl-[3-(4',5'-difluoro-2'-methoxy-biphenyl-4-yloxymethyl)-phenyl]-amino}-acetic acid ethyl ester as a clear film (10 mg, 21%). LC-MS (ES) calculated for C26H25F2NO5, 469.17; found m/z 470 [M+H]$^+$.

To a round bottom flask containing {acetyl-[3-(4',5'-difluoro-2'-methoxy-biphenyl-4-yloxymethyl)-phenyl]-amino}-acetic acid ethyl ester (10 mg, 0.02 mmol) was added lithium hydroxide hydrate (2 mg, 0.05 mmol), tetrahydrofuran (0.5 mL) and water (0.5 mL). The reaction was stirred at room temperature overnight, diluted with ethyl acetated (25 mL) and washed with aqueous HCl (0.1 M, 25 mL) and brine (25 mL), dried over magnesium sulfate, concentrated and dried from hexanes/methylene chloride mixtures to yield {acetyl-[3-(4',5'-difluoro-2'-methoxy-biphenyl-4-yloxymethyl)-phenyl]-amino}-acetic acid as an off white solid (12 mg, 127%) LC-MS (ES) calculated for C24H21F2NO5, 441.14; found m/z 442 [M+H]+.

Example 10

N-[3-(2',4',5'-Trifluoro-biphenyl-4-yloxymethyl)-phenyl]-methanesulfonamide

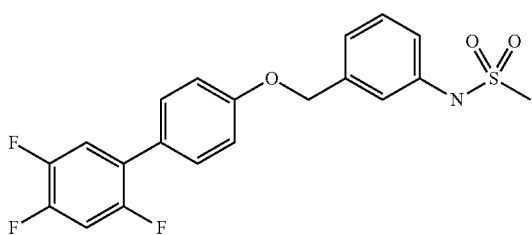

A solution of 2,4,5-trifluoro-4'-(3-nitro-benzyloxy)-biphenyl (150 mg, 0.418 mmol) and 10% Pd/C (40 mg) in EtOAc (2 mL), EtOH (10 mL) and 6N HCl (100 uL) was hydrogenated at 50 psi for 1.25 hrs. The reaction mixture was filtered through Celite and evaporated to dryness to give 3-(2',4',5'-trifluoro-biphenyl-4-yloxymethyl)-phenylamine hydrochloride. LC-MS (ES) calculated for C19H14F3NO, 329.32; found m/z 330 [M+H]+.

A solution of 3-(2',4',5'-trifluoro-biphenyl-4-yloxymethyl)-phenylamine hydrochloride (76 mg, 0.209 mmol), triethylamine (29 uL, 0.209 mmol) and methanesulfonyl chloride (19.3 uL, 0.249 mmol) in dry pyridine (3 mL) was stirred at ice bath temperature for 1 hr and then at RT for 2 hrs. The reaction mixture was evaporated, re-evaporated from toluene, dissolved in EtOAc, washed with H2O, dried over MgSO4, filtered and concentrated. The crude product was purified by flash chromatography with a 0-25% gradient of ethyl acetate in hexanes and lyophilized to yield 48 mg of N-[3-(2',4',5'-trifluoro-biphenyl-4-yloxymethyl)-phenyl]-methanesulfonamide as a white amorphous powder. LC-MS (ES) calculated for C20H16F3NO3S, 407.41; found m/z 406 [M−H]−.

Example 11

N-[3-(4',5'-Difluoro-2'-methoxy-biphenyl-4-yloxymethyl)-phenyl]-methanesulfonamide

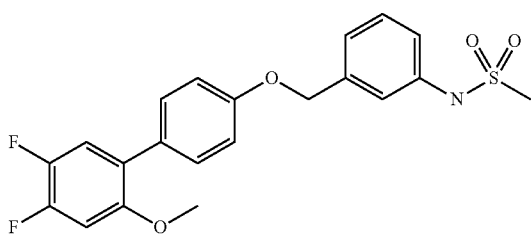

A solution of 4,5-difluoro-2-methoxy-4'-(3-nitro-benzyloxy)-biphenyl (300 mg, 0.808 mmol) and 10% Pd/C (45 mg) in EtOAc (2 mL), EtOH (13 mL) and 6N HCl (150 uL) was hydrogenated at 50 psi for 1.5 hrs. The reaction mixture was filtered through Celite and evaporated to dryness to give 289 mg (95%) of 3-(4',5'-difluoro-2'-methoxy-biphenyl-4-yloxymethyl)-phenylamine hydrochloride. LC-MS (ES) calculated for C20H17F2NO2, 341.36; found m/z 342 [M+H]+.

A solution of 3-(4',5'-difluoro-2'-methoxy-biphenyl-4-yloxymethyl)-phenylamine hydrochloride (101 mg, 0.269 mmol), triethylamine (38 uL, 0.269 mmol) and methanesulfonyl chloride (27 uL, 0.349 mmol) in dry pyridine (4 mL) was reacted similar to N-[3-(2',4',5'-trifluoro-biphenyl-4-yloxymethyl)-phenyl]-methanesulfonamide above. The crude product was purified by flash chromatography with a 0-15% gradient of ethyl acetate in hexanes to yield 60 mg of N-[3-(4',5'-difluoro-2'-methoxy-biphenyl-4-yloxymethyl)-phenyl]-methanesulfonamide as a white solid. LC-MS (ES) calculated for C21H19F2NO4S, 419.45; found m/z 418 [M−H]−.

Example 12

C,C,C-Trifluoro-N-[3-(2',4',5'-trifluoro-biphenyl-4-yloxymethyl)-phenyl]methanesulfonamide

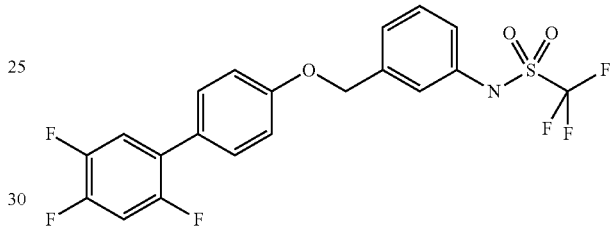

A solution of 3-(2',4',5'-trifluoro-biphenyl-4-yloxymethyl)-phenylamine hydrochloride (76 mg, 0.209 mmol), triethylamine (29 uL, 0.209 mmol) and trifluoromethanesulfonic anhydride (500 uL) in dry pyridine (3 mL) was reacted as for N-[3-(2',4',5'-trifluoro-biphenyl-4-yloxymethyl)-phenyl]-methanesulfonamide above. The crude product was purified by flash chromatography with a 0-10% gradient of ethyl acetate in hexanes to yield 17 mg (18%) of C,C,C-trifluoro-N-[3-(2',4',5'-trifluoro-biphenyl-4-yloxymethyl)-phenyl]methanesulfonamide as a white amorphous powder. LC-MS (ES) calculated for C20H13F6NO3S, 461.39; found m/z 460 [M−H]−.

Example 13

N-[3-(4',5'-Difluoro-2'-methoxy-biphenyl-4-yloxymethyl)-phenyl]-C,C,C-trifluoromethanesulfonamide

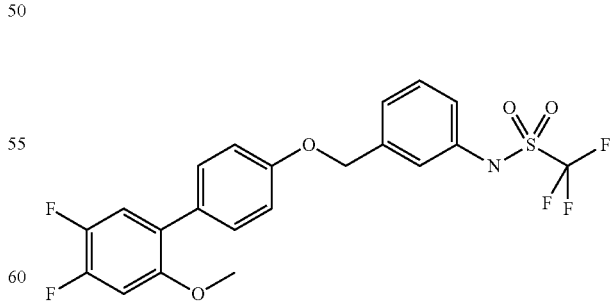

A solution of 3-(4',5'-trifluoro-2'-methoxy-biphenyl-4-yloxymethyl)-phenylamine hydrochloride (101 mg, 0.269 mmol), triethylamine (75 uL, 0.538 mmol) and trifluoromethanesulfonic anhydride (226 uL, 1.345 mmol) in dry pyridine (5 mL) was reacted as for C,C,C-trifluoro-N-[3-(2', 4',5'-trifluoro-biphenyl-4-yloxymethyl)-phenyl]methanesulfonamide above. The crude product was purified by flash chromatography with a 0-10% gradient of ethyl acetate in hexanes and lyophilized to yield 48 mg (37.7%) of N-[3-(4', 5'-difluoro-2'-methoxy-biphenyl-4-yloxymethyl)-phenyl]-C,C,C-trifluoromethanesulfonamide as a white amorphous powder. LC-MS (ES) calculated for C21H16F5NO4S, 473.42; found m/z 472 [M−H]⁻.

Example 14

Glycogen Synthase (GS) Assay

The following tests were carried out in order to determine the activity of the compounds of formula (I).

Twelve μL per well of substrate solution containing glycogen (4.32 mg/'ml), 2.67 mM UDP-glucose, 21.6 mM phospho(enol)pyruvate and 2.7 mM NADH in 30 mM glycylglycine, pH 7.3 buffer was added into a polystyrene 384-well assay plate (BD Biosciences).

Compound solutions (8 μL/well) at various concentrations (0-300 μM) were added to the assay plate (columns 5-24). Compound solution contains 30 mM glycylglycine, pH 7.3, 40 mM KCl, 20 mM $MgCl_2$, 9.2% DMSO, with (columns 15-24) or without (columns 5-14) 20 mM glucose 6-phosphate.

Enzyme solution (12 μL/well) containing glycogen synthase (16.88 μg/ml), pyruvate kinase (0.27 mg/ml), lactate dehydrogenase (0.27 mg/ml) in 50 mM Tris-HCl, pH 8.0, 27 mM DTT and bovine serum albumin (BSA, 0.2 mg/ml) was added to the assay plate (columns 3-24). As a blank control, enzyme solution without glycogen synthase was added into the top half wells of columns 1-2. To the bottom half wells of columns 1-2 were added a known activator, glucose 6-phosphate (at final concentration 5 mM) in addition to the enzyme solution. The reaction mixture was incubated at room temperature. The assay plate was then read for absorbance at 340 nm on an Envision reader every 3 minutes up to a total of 15 minutes.

The enzyme activity (with or without compound) was calculated by the reaction rate and represented by the optical density change (SOD) per minute. Percent stimulation of glycogen synthase activity by a compound at various concentrations was calculated by the following formula:

% stimulation=100*$Rs/Rt$,

Where Rs is the reaction rate of the enzyme in the presence of compound and Rt is the reaction rate of the enzyme in the absence of compound.

$SC_{200}$ is defined as the compound concentration that is needed to stimulate 200% of the enzyme activity. $EC_{50}$ is defined as the compound concentration that is needed to give 50% maximum activation.

Compounds from Example 1 through Example 13 were assayed according to assay procedures described above and the results are listed in Table 1:

TABLE 1

Glycogen Synthase Activation Potency of Exemplified Compounds

| Example Number | GS $SC_{200}$ (μM) | GS $EC_{50}$ (μM) |
|---|---|---|
| 1 | 2.69 | 6.96 |
| 2 | 3.24 | 5.93 |
| 3 | 1.3 | 4.4 |
| 4 | 2.09 | 6.15 |
| 5 | 0.65 | 2.84 |

TABLE 1-continued

Glycogen Synthase Activation Potency of Exemplified Compounds

| Example Number | GS $SC_{200}$ (μM) | GS $EC_{50}$ (μM) |
|---|---|---|
| 6 | 0.77 | 3.14 |
| 7 | 0.7 | 3.71 |
| 8 | 2.43 | 6.37 |
| 9 | 0.33 | 1.02 |
| 10 | 2.41 | 5.71 |
| 11 | 1.1 | 2.75 |
| 12 | 0.95 | 1.48 |
| 13 | 0.18 | 0.44 |

It is to be understood that the invention is not limited to the particular embodiments of the invention described above, as variations of the particular embodiments may be made and still fall within the scope of the appended claims.

What is claimed is:

1. A compound of Formula (I):

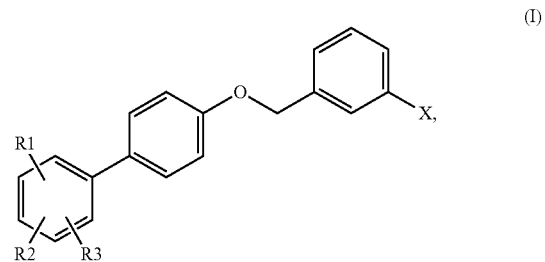

(I)

wherein:
R1, R2, R3, independently or each other, is hydrogen, halogen, lower alkyl or alkoxy;
X is —NR4R5, unsubstituted pyrollidine or pyrollidine substituted with acid;
R4 is hydrogen, lower alkyl or an acyl moiety; and
R5 is an acyl moiety, —$CH_2COOH$, or —$SO_2$-lower alkyl unsubstituted or mono-, bi- or trisubstituted with halogen;

or a pharmaceutically acceptable salt thereof.

2. The compound according to claim 1, wherein R1, R2, R3, independently of each other, is hydrogen, halogen, lower alkyl or alkoxy; and X is —NR4R5.

3. The compound according to claim 1, wherein R1, R2, R3, independently of each other, is hydrogen, halogen, lower alkyl or alkoxy; and X is unsubstituted pyrollidine or pyrollidine substituted with acid.

4. The compound according to claim 1, wherein R4 is hydrogen, lower alkyl or acyl moiety; and R5 is an acyl moiety, —$CH_2COOH$, or —$SO_2$-lower alkyl unsubstituted or mono-, bi- or trisubstituted with halogen.

5. The compound according to claim 1, wherein R4 is an acyl moiety and R5 is an acyl moiety.

6. The compound according to claim 1, wherein R4 is hydrogen and R5 is an acyl moiety.

7. The compound according to claim 1, wherein R4 is hydrogen and R5 is —$SO_2$-lower alkyl unsubstituted or mono-, bi- or trisubstituted with halogen.

8. The compound according to claim 1, wherein X is —NR4R5.

9. The compound according to claim 1, wherein X is unsubstituted pyrollidine or pyrollidine substituted with an acid.

10. The compound according to claim 1, wherein X is unsubstituted pyrollidine.

11. The compound according to claim 1, wherein X is pyrollidine substituted with carboxylic acid or acetic acid.

12. The compound according to claim 1, wherein R1, R2, R3, independently of each other, is hydrogen, fluoro, chloro, methyl or methoxy.

13. The compound according to claim 1, wherein R1 is hydrogen or fluoro.

14. The compound according to claim 1, wherein R2 if fluoro.

15. The compound according to claim 1, wherein R3 is fluoro or methoxy.

16. The compound according to claim 1, wherein R4 is hydrogen or —C(O)CH$_3$.

17. The compound according to claim 1, wherein R4 is hydrogen.

18. The compound according to claim 1, wherein R5 is an acyl moiety.

19. The compound according to claim 1, wherein R5 is —C(O)(CH$_2$)$_2$COOH or —C(O)-cycloalkyl.

20. The compound according to claim 1, wherein R5 is —C(O)-cyclopentane, unsubstituted or substituted with —COOH.

21. The compound according to claim 1, wherein R5 is —CH$_2$COOH or —SO$_2$-lower alkyl unsubstituted or mono-, bi- or trisubstituted with halogen.

22. The compound according to claim 1, wherein R5 is —SO$_2$CH$_3$ or —SO$_2$CF$_3$.

23. The compound according to claim 1, wherein said compound is:

N-[3-(2',4'-Difluoro-biphenyl-4-yloxymethyl)-phenyl]-succinamic acid;
(trans)-2-[3-(2',4'-Difluoro-biphenyl-4-yloxymethyl)-phenylcarbamoyl]-cyclopentanecarboxylic acid;
(1R,2R)-2-[3-(2',4'-Difluoro-biphenyl-4-yloxymethyl)-phenylcarbamoyl]-cyclopentanecarboxylic acid;
(1S,2S)-2-[3-(2',4'-Difluoro-biphenyl-4-yloxymethyl)-phenylcarbamoyl]-cyclopentanecarboxylic acid;
(1R,2S)-2-[3-(2',4'-Difluoro-biphenyl-4-yloxymethyl)-phenylcarbamoyl]-cyclopentanecarboxylic acid;
(1S,2R)-2-[3-(2',4'-Difluoro-biphenyl-4-yloxymethyl)-phenylcarbamoyl]-cyclopentanecarboxylic acid;
(S)-1-[3-(4',5'-Difluoro-2'-methoxy-biphenyl-4-yloxymethyl)-phenyl]-pyrrolidine-2-carboxylic acid;
{(S)-1-[3-(4',5'-Difluoro-2'-methoxy-biphenyl-4-yloxymethyl)-phenyl]-pyrrolidin-2-yl}-acetic acid;
{Acetyl-[3-(4',5'-difluoro-2'-methoxy-biphenyl-4-yloxymethyl)-phenyl]-amino}-acetic acid;
N-[3-(2',4',5'-Trifluoro-biphenyl-4-yloxymethyl)-phenyl]-methanesulfonamide;
N-[3-(4',5'-Difluoro-2'-methoxy-biphenyl-4-yloxymethyl)-phenyl]-methanesulfonamide;
C,C,C-Trifluoro-N-[3-(2',4',5'-trifluoro-biphenyl-4-yloxymethyl)-phenyl]methanesulfonamide; and
N-[3-(4',5'-Difluoro-2'-methoxy-biphenyl-4-yloxymethyl)-phenyl]-C,C,C-trifluoromethanesulfonamide.

24. A pharmaceutical composition, comprising a therapeutically effective amount of a compound according to claim 1 and a pharmaceutically acceptable carrier and/or adjuvant.

* * * * *